(12) United States Patent
Shao et al.

(10) Patent No.: US 8,383,830 B2
(45) Date of Patent: *Feb. 26, 2013

(54) CYANINE COMPOUNDS AND THEIR USE IN STAINING BIOLOGICAL SAMPLES

(75) Inventors: Jianhui Shao, Nanshan Shenzhen (CN); Bing Xu, Nanshan Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 641 days.

This patent is subject to a terminal disclaimer.

(21) Appl. No.: 12/607,614

(22) Filed: Oct. 28, 2009

(65) Prior Publication Data

US 2010/0112584 A1 May 6, 2010

(30) Foreign Application Priority Data

Oct. 31, 2008 (CN) .......................... 2008 1 0217140

(51) Int. Cl.
  *C07D 403/08* (2006.01)
  *C07D 413/08* (2006.01)
  *C07D 417/08* (2006.01)

(52) U.S. Cl. .................... 548/159; 548/217; 548/305.1; 548/468

(58) Field of Classification Search ........................ None
See application file for complete search history.

(56) References Cited

U.S. PATENT DOCUMENTS

| | | |
|---|---|---|
| 4,882,284 A | 11/1989 | Kirchanski et al. |
| 5,155,044 A | 10/1992 | Ledis et al. |
| 5,196,346 A | 3/1993 | Lefevre et al. |
| 5,264,369 A | 11/1993 | Sakata et al. |
| 5,298,426 A | 3/1994 | Inami et al. |
| 5,308,772 A | 5/1994 | Sakata et al. |
| 5,413,938 A | 5/1995 | Tsujino et al. |
| 5,516,695 A | 5/1996 | Kim et al. |
| 5,518,928 A | 5/1996 | Cremins et al. |
| 5,538,893 A | 7/1996 | Sakata et al. |
| 5,559,037 A | 9/1996 | Kim et al. |
| 5,618,733 A | 4/1997 | Sakata et al. |
| 5,648,225 A | 7/1997 | Kim et al. |
| 5,677,183 A | 10/1997 | Takarada et al. |
| 5,874,310 A | 2/1999 | Li et al. |
| 5,879,900 A | 3/1999 | Kim et al. |
| 5,917,584 A | 6/1999 | Li et al. |
| 5,958,776 A | 9/1999 | Sakata et al. |
| 6,197,851 B1 | 3/2001 | Maxwell et al. |
| 6,214,625 B1 | 4/2001 | Li et al. |
| 6,368,864 B1 | 4/2002 | Deka et al. |
| 6,410,330 B1 | 6/2002 | Li et al. |
| 6,472,215 B1 | 10/2002 | Huo et al. |
| 6,551,831 B2 | 4/2003 | Gupta et al. |
| 6,573,102 B2 | 6/2003 | Li et al. |
| 6,664,110 B1 | 12/2003 | Tsuji et al. |
| 6,673,618 B1 | 1/2004 | Li et al. |
| 6,911,313 B2 | 6/2005 | Houwen et al. |
| 6,916,658 B2 | 7/2005 | Li et al. |
| 7,008,792 B2 | 3/2006 | Lopez et al. |
| 7,049,093 B2 | 5/2006 | Tsuji et al. |
| 7,208,319 B2 | 4/2007 | Lopez et al. |
| 2002/0022004 A1 | 2/2002 | Licha et al. |
| 2003/0219850 A1 | 11/2003 | Tsuji et al. |
| 2004/0241770 A1 | 12/2004 | Houwen et al. |
| 2005/0208534 A1 | 9/2005 | Dallwig et al. |
| 2006/0275801 A1 | 12/2006 | Henkin et al. |
| 2006/0292658 A1 | 12/2006 | Lynch |
| 2007/0178597 A1 | 8/2007 | Tsuji et al. |
| 2007/0203343 A1 | 8/2007 | West et al. |
| 2007/0287145 A1 | 12/2007 | Mizukami et al. |
| 2007/0298408 A1 | 12/2007 | Mizukami et al. |
| 2008/0153170 A1 | 6/2008 | Garrett et al. |
| 2010/0143955 A1* | 6/2010 | Baohua et al. .................. 435/14 |
| 2011/0136242 A1* | 6/2011 | Marx et al. ...................... 436/71 |
| 2011/0159483 A1 | 6/2011 | Zhao et al. |

FOREIGN PATENT DOCUMENTS

| | | |
|---|---|---|
| CN | 1364829 | 8/2002 |
| CN | 1637077 | 12/2004 |

(Continued)

OTHER PUBLICATIONS

Chen Xin, Yao Zu-Guang, "Synthesis and Properties of N-Benzylindotricarbocyanine Dyes". Chemical Journal of Chinese Universities, vol. 17, No. 10, 1996, pp. 1613-1616.

(Continued)

*Primary Examiner* — Rebecca Anderson
*Assistant Examiner* — Michael Barker
(74) *Attorney, Agent, or Firm* — Kory D. Christensen; Matthew S. Bethards; Stoel Rives LLP

(57) ABSTRACT

Cyanine compounds having the general formula I for staining biological samples, wherein $R_1$, $R_2$, X, Y, $A_1$ and $A_2$ are as defined in the specification. These kinds of compounds may show good light illumination stability, have a maximum absorption peak around 640 nm that may not change as a function of ambient temperature, have rapidly increased fluorescence intensity upon binding to nucleic acids to form compound/nucleic acid complexes, and have a light spectrum in the near-infrared region, thereby effectively reducing interference from background fluorescence and increasing the accuracy of the detection when used as a staining agent for nucleic acids in a flow cytometer. The compounds provided can be used as a staining agent for erythroblasts in the blood.

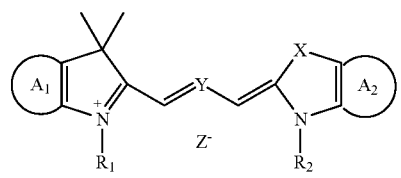

27 Claims, 8 Drawing Sheets

FOREIGN PATENT DOCUMENTS

| | | |
|---|---|---|
| CN | 1939978 | 9/2005 |
| WO | WO 2005108405 A2 * | 11/2005 |
| WO | WO 2008/040994 | 4/2008 |

OTHER PUBLICATIONS

Mujumadar et al., "Cyanine Dye Labeling Reagents: Sulfoindocyanine Succinimidyl Esters." Biocojugate Chemistry, vol. 4, No. 2, 1993, pp. 105-111.

U.S. Appl. No. 12/633,452, filed Dec. 8, 2009, Baohua et al.

Tatarets et al., 'Synthesis of Water-Soluble, Ring-Substituted Squaraine Dyes and their Evaluation as Fluorescent Probes and Labels', Analytica Chimica Acta, 570(2), pp. 214-223, 2006.

Ioffe et al., 'A New Fluorescent Squaraine Probe for the Measurement of Membrane Polarity', Journal of Fluorescence, 16(1), pp. 47-52, 2006.

Oswald et al., 'Synthesis, Spectral Properties, and Detection Limits of Reactive Squaraine Dyes, a New Class of Diode Laser Compatible Fluorescent Protein Labels', Bioconjugate Chem, 10, pp. 925-931, 1999.

Office Action dated Jun. 25, 2012 for U.S. Appl. No. 12/633,452.

Restriction Requirement dated Mar. 28, 2012 for U.S. Appl. No. 12/633,452.

Office Action dated Apr. 24, 2012 for U.S. Appl. No. 12/826,231.

Notice of Allowance and Fees Due dated Aug. 1, 2012 for U.S. Appl. No. 12/826,231.

Notice of Allowance dated Oct. 30, 2012 for U.S. Appl. No. 12/633,452.

* cited by examiner

CYANINE COMPOUNDS AND THEIR USE IN STAINING BIOLOGICAL SAMPLES

RELATED APPLICATIONS

This application claims priority to Chinese Patent Application No. 200810217140.9, filed Oct. 31, 2008, for "CYANINE COMPOUNDS AND THEIR USES IN STAINING BIOLOGICAL SAMPLES," the disclosure of which is fully incorporated herein by reference.

TECHNICAL FIELD

The present disclosure relates to the field of fluorescent dye compounds, more particularly to cyanine compounds.

BRIEF SUMMARY

The present disclosure relates to fluorescent dyes. More particularly, the present disclosure relates to cyanine compounds applicable to staining biological samples, compositions comprising said cyanine compounds, and their use in staining biological samples.

DETAILED DESCRIPTION

Figure 1:
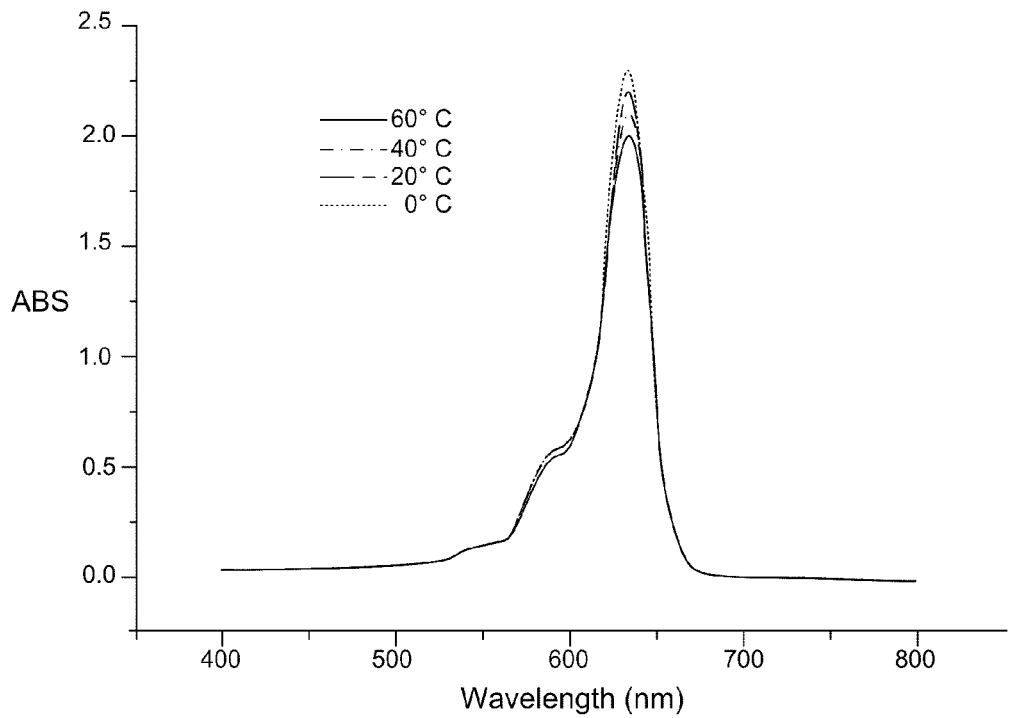
FIG. 1 shows absorption spectra of the exemplary Dye-1 compound after being placed at different ambient temperatures for 48 hours. The instrument used is a UVmini-1240 UV-Vis Spectrophotometer.

Erythroblasts (or nucleated red blood cells, NRBC) are immature erythrocytes and can be classified into early, intermediate and late erythroblasts. They are normally present in hematopoietic tissues and organs such as bone marrow. The increase in the number of erythroblasts in peripheral blood may be a physiological and pathological compensatory response to anemia, hypoxia, etc., in the body. Recent studies confirm that there exists a small number of fetal erythroblasts in the maternal peripheral blood. It is also discovered that under certain pathological states during pregnancy, such as fever, pregnancy-induced hypertension syndrome, fetal intrauterine hypoxia, etc., there are cases that the number of fetal erythroblasts increases in the maternal peripheral blood. Therefore, the detection of erythroblasts is of clinical importance.

Conventionally, erythroblasts are clinically analyzed and identified by manual microscopic examination. This approach is time-consuming and largely depends on the experience and subjective judgment of the observer.

In the 1970's, Flow Cytometry (FCM) was developed. This technology uses the flow cytometer to conduct quantitative, rapid, objective and multi-parameter detection and analysis on biological particles like cells. Automatic blood analyzers utilize flow cytometry and the nuclear staining technique to distinguish erythroblasts from other cell types. Thus, the differentiation and counting of blood cells can be performed in common examination rooms, which enhances the efficiency of detection.

U.S. Pat. No. 5,298,426 discloses a fluorescence method for analyzing erythroblasts in two steps. This two-step method decreases the efficiency of detection.

U.S. Pat. No. 5,559,037 proposes a method for analyzing erythroblasts and leukocytes based on flow cytometry. The nucleic acid dye used in this method is ethidium bromide. The complexes formed by ethidium bromide with the nucleic acids are susceptible to optical bleaching during light illumination. Moreover, this substance is carcinogenic and less sensitive, which poses certain threats to the operators of the instrument and to the environment.

U.S. Pat. No. 5,879,900 discloses a method for differentiating erythroblasts, damaged leukocytes and leukocytes in the blood based on flow cytometry. The method comprises first adding fluorescently labeled antibodies into the blood sample to be detected, which results in increased cost of detection and complicated steps of detection.

U.S. Pat. No. 6,197,593 proposes a method that utilizes the SYTO series as the nucleic acid dye for differentiating reticulocytes, erythroblasts and erythrocytes in the blood sample. The synthesis process for this series of dyes is long.

Therefore, there is need to continue to develop novel fluorescent dyes to meet the requirements for detecting biological samples accurately and rapidly.

In one aspect of the present disclosure there is provided a compound having the general formula I:

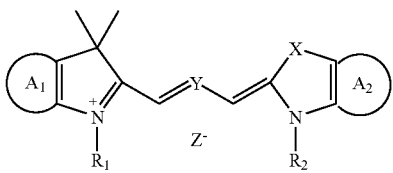

wherein

R₁ and R₂ are each independently selected from at least one of the following: $C_{1-18}$alkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that R₁ and R₂ are not all simultaneously benzyl;

R₆ in each occurrence is independently selected from at least one of the following: H, $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is —CH—CH=CH—,

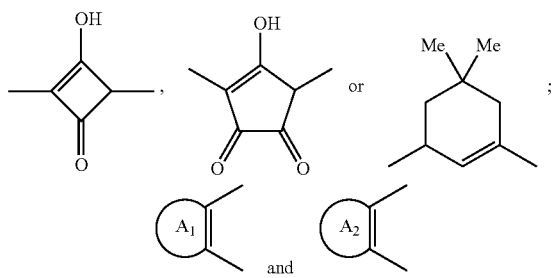

and are each independently selected from

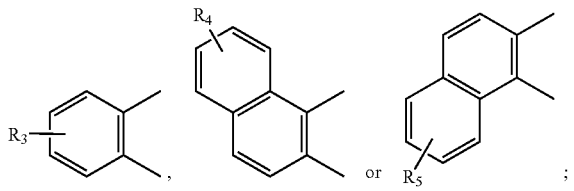

R₃, R₄ and R₅ are each independently selected from at least one of the following: H, halogen, cyano, hydroxyl, $C_{1-18}$alkyl, $C_{1-18}$alkylsulphonyl, sulphonyl and $C_{1-5}$alkylCOOR$_7$;

R₇ is H or $C_{1-6}$alkyl; and

Z⁻ is an anion.

In one embodiment, when Y is —CH—CH=CH—, A₁ and A₂ are simultaneously

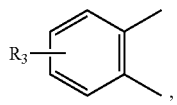

R₃ are not simultaneously sulfonate group for both A₁ and A₂.

In another aspect of the present disclosure there is provided a conjugate comprising the above-said compound having the general formula I.

In yet another aspect of the present disclosure there is provided a composition for staining biological samples, said composition comprising the above-said compound having the general formula I or the conjugate thereof.

In still another aspect of the present disclosure there is provided a use of the above-said compound having the general formula I or the conjugate thereof in staining biological samples.

The compounds according to the present disclosure may have the following properties: (1) emitting little or no fluorescence when unbound to nucleic acids but having rapidly increased fluorescence intensity upon forming complexes with nucleic acids; and having a light spectrum in the near-infrared region, thereby avoiding interference from background fluorescence and increasing the accuracy of the detection results; (2) useful as staining agents for various biological samples on a flow cytometer; (3) capable of being excited at about 640 nm, with its wavelength remaining stable at 40° C., thereby matching the working wavelength of the semiconductor laser used; (4) having good light illumination stability, being rapidly degradable in aqueous solutions and more favorable to both the operators of the instrument and the environment; and (5) having a short synthesis process, readily available raw materials and low cost.

These and other features of the present disclosure will become apparent by reference to the following drawings and specific embodiments of the present disclosure.

Definitions

Unless otherwise specified, the terms as used herein have the following meanings.

The term "alkyl" as used herein individually or in combination with other groups refers to straight or branched alkyl groups containing 1-18 carbon atoms, such as 1-12, or alternatively 1-8, or 1-6 carbon atoms. Reference to a single straight alkyl such as "n-propyl" specifically means a straight alkyl group, while reference to a single branched alkyl such as "isopropyl" specifically means a branched alkyl group. For example, "$C_{1-6}$alkyl" includes $C_{1-4}$alkyl, $C_{1-3}$alkyl, methyl, ethyl, n-propyl, isopropyl and tert-butyl. The same rules apply to other groups as used throughout the present specification.

The term "halogen" as used herein includes fluorine, chlorine, bromine and iodine.

The term "biological sample" as used herein includes, but is not limited to, peptides, proteins, nucleic acids, and erythroblasts in the blood.

The term "aryl" as used herein refers to an aromatic monocyclic group or an aromatic fused 2 or 3 ring group containing 3 to 20 carbon atoms, also optionally containing 1 to 3 heteroatoms selected from N, O and S.

The term "heterocyclyl" as used herein refers to a non-aromatic monocyclic group or a non-aromatic fused 2 or 3 ring group containing 3 to 20 carbon atoms, also optionally containing 1 to 3 heteroatoms selected from N, O and S.

The term "sulphonyl" as used herein refers to the —SO₃H group or the —SO₃⁻M group, wherein M is a counterion including such ions as alkali metal ions (e.g., K+ ion) or alkaline earth metal ions.

The term "alkylsulphonyl" as used herein refers to a group in which the "sulphonyl" as defined above is attached to the other part of the molecule via the "alkyl" as defined above.

Compounds According to the Present Disclosure

In one aspect of the present disclosure there is provided a compound having the general formula I:

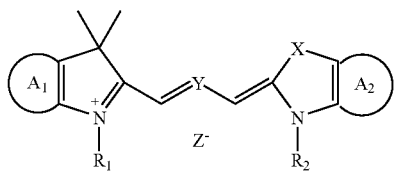

wherein $R_1$ and $R_2$ are each independently selected from at least one of the following: $C_{1-18}$alkylCOOR$_6$, $C_{1-18}$alkylOR$_6$ and benzyl, wherein said benzyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;

$R_6$ in each occurrence is independently selected from at least one of the following: H, $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is —CH—CH=CH—

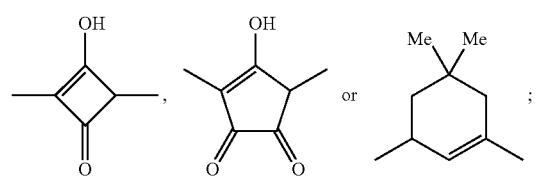

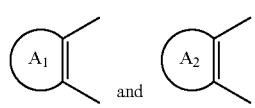

are each independently selected from

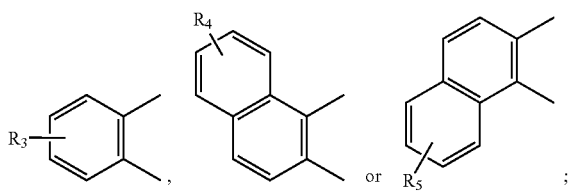

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkylCOOR$_7$;

$R_7$ is H or $C_{1-6}$alkyl;

$Z^-$ is an anion.

In one embodiment, when Y is —CH—CH=CH—, $A_1$ and $A_2$ are simultaneously

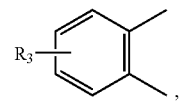

$R_3$ are not simultaneously sulfonate group for both $A_1$ and $A_2$.

In one embodiment, $R_1$ and $R_2$ are each independently selected from at least one of the following: $C_{1-6}$alkylCOOR$_6$, $C_{1-6}$alkylOR$_6$ and benzyl, provided that $R_1$ and $R_2$ are not all simultaneously benzyl.

In one embodiment, $R_6$ in each occurrence is independently selected from H, $C_{1-6}$alkyl or phenyl.

In one embodiment, $R_3$, $R_4$ and $R_5$ are each independently selected from at least one of the following: H, halogen, cyano, hydroxyl, $C_{1-6}$alkyl, $C_{1-6}$alkylsulphonyl, sulphonyl or $C_{1-5}$alkylCOOR$_7$, provided that $R_3$ are not simultaneously sulfonate group when Y is —CH—CH=CH—, $A_1$ and $A_2$ are simultaneously

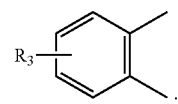

In one embodiment, X is $C(CH_3)_2$, O or S.

In one embodiment,

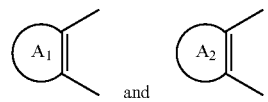

are each independently selected from

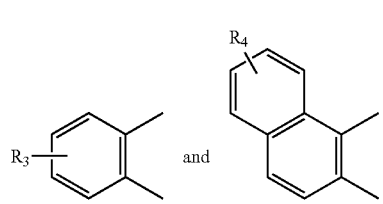

In one embodiment, $Z^-$ is selected from halogen ions, $ClO_4^-$, $PF_6^-$, $CF_3SO_3^-$, $BF_4^-$, acetate or p-toluenesulfonate anions.

In one embodiment, the compound of formula I is selected from Dye-1, Dye-2, Dye-3, Dye-4, Dye-5, or Dye-6, wherein such dyes have the following structures:

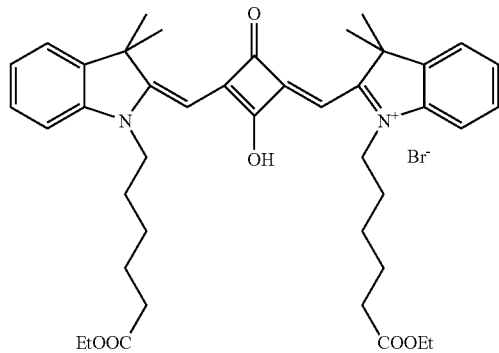

DYE-1

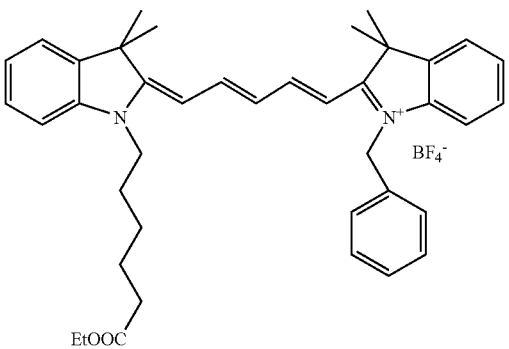

DYE-2

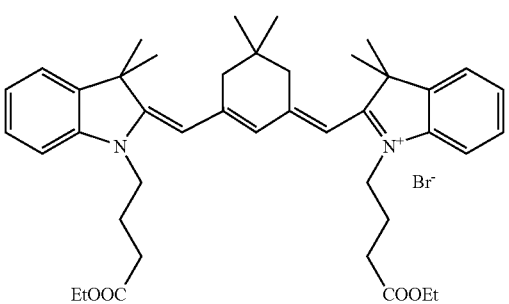

DYE3

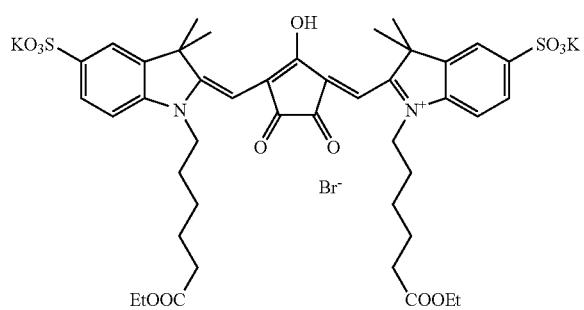

DYE-4

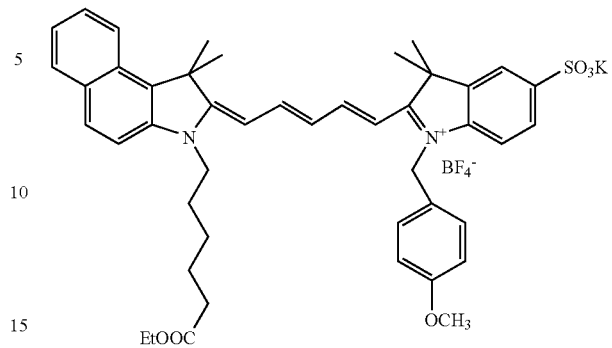

DYE-5

DYE-6

In some embodiments, the compound according to the present disclosure can be directly used for staining biological samples in the form of salts as described herein. Alternatively, in one embodiment, the compound according to the present disclosure in some examples can be used in the form of derivatives of the compound having the general formula I, said derivatives including, but not limited to, conjugates.

Typically, conjugates are used in the fluorescence activated cell sorter (FACS). "Conjugate" as used herein refers to the compound formed by attaching the compound according to the present disclosure to other molecules via covalent bonds. Molecules that can be conjugated with the compound according to the present disclosure may be those that specifically bind to cells or cell components, including, but not limited to, antibodies, antigens, receptors, ligands, enzymes, substrates, coenzymes or the like. Generally, the sample to be detected is incubated with a conjugate for a period of time so that the conjugate binds specifically to certain cells or cell components in the sample to be detected. The binding of the conjugate to the cells or cell components can also be referred to as staining. The above staining steps can be repeated in sequence for several times, or a variety of conjugates can be used for concurrent multistaining. At the completion of staining, the sample is analyzed in the fluorescence activated cell sorter wherein the excitation light source excites the compound according to the present disclosure in the conjugate and the detection apparatus detects the emitted light generated by the excited compound.

Alternatively, in another embodiment, the conjugates can also be used in solid phase immunological assays, e.g. sandwich immunological assays. The techniques of solid phase immunological assays are well-known in the art and can be found in standard textbooks. Said conjugates can be used as various suitable components in solid phase immunological assays.

The Process for Preparing the Compound According to the Present Disclosure

The compounds according to the present disclosure can be synthetically obtained using the general methods well known in the art. In particular, some of the intermediates of the compounds according to the present disclosure can be synthetically obtained by the following process.

The unsubstituted or substituted compound of the formula II or III is used as the raw material to react with the halide of the formula $R_1X$ or $R_2X$ (X is F, Cl, Br or I):

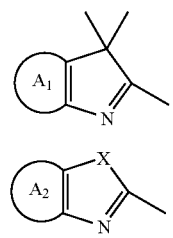

Formula II

Formula III to obtain the quaternary ammonium salt intermediate of the formula IV or formula V:

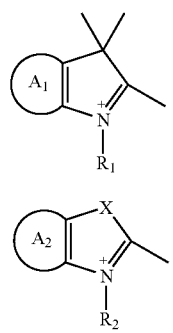

Formula IV

Formula V wherein $R_1$, $R_2$, X, A1 ring and A2 ring are respectively as defined above for the compound having the general formula I.

For example, the following reactions yield the corresponding quaternary ammonium salt intermediates.

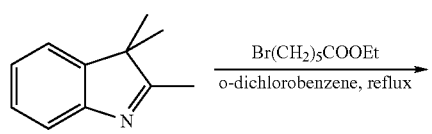

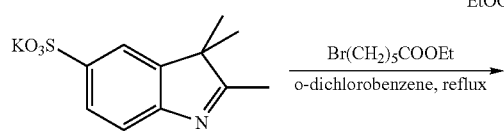

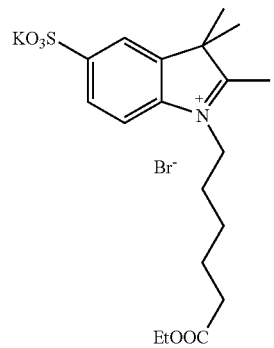

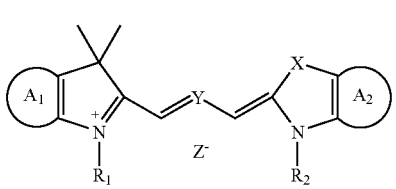

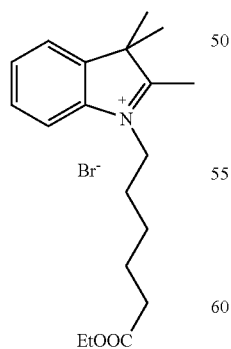

Then, the thus obtained quaternary ammonium salt intermediate of the formula IV or formula V is condensed with a linker molecule to obtain the compound having the general formula I:

Formula I

Wherein X, Y, $R_1$, $R_2$, $Z^-$, A1 ring and A2 ring are as defined above, and the linker molecule can be squaric acid, isophorone, etc.

For example, some of the target compounds according to the present disclosure can be synthesized through the following process:

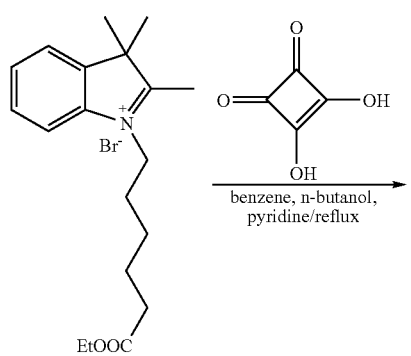

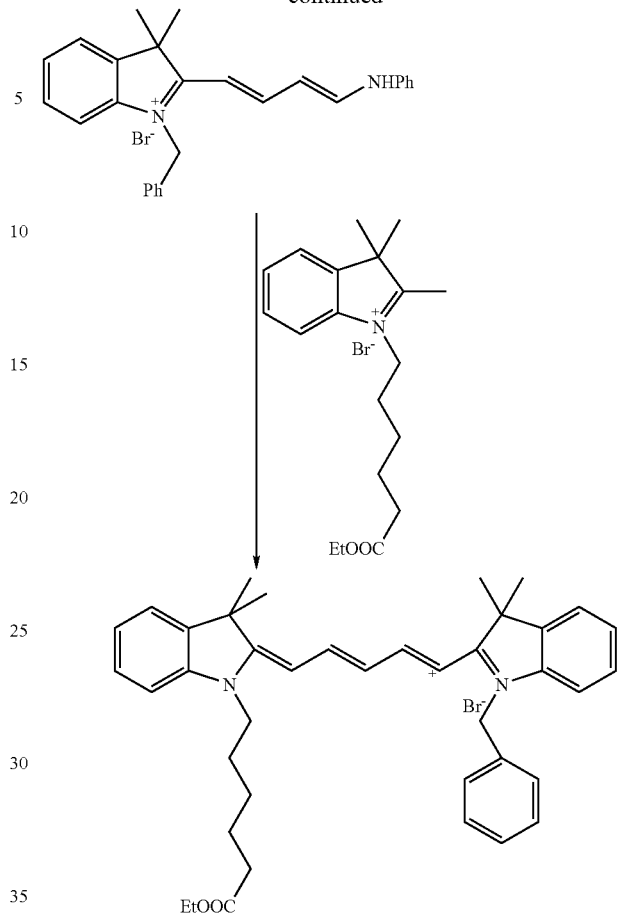

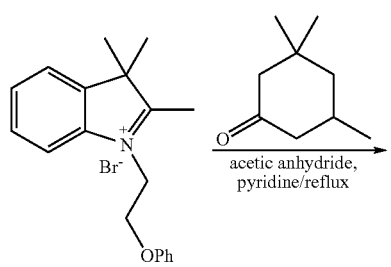

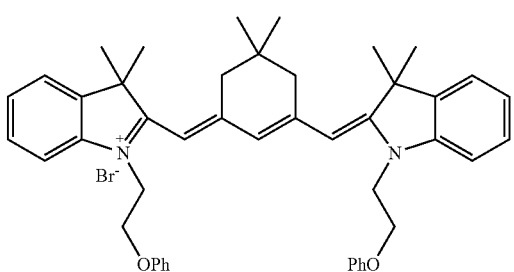

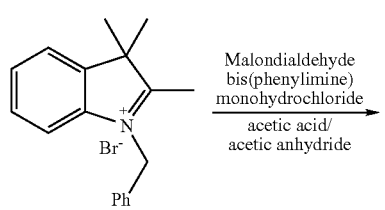

The resulting compounds can be recovered using the separation and purification techniques well known in the art to achieve the desired purity.

The raw materials used in the present disclosure are commercially available, or can be readily prepared from raw materials known in the art using methods known to those skilled in the art or methods disclosed in the prior art.

The Composition of the Present Disclosure

In one embodiment according to the present disclosure, a composition for staining biological samples is further provided, which comprises the above-said compound having the general formula I or the conjugate thereof.

Said biological samples are selected from peptides, proteins, nucleic acids, and erythroblasts in the blood. Said proteins are selected from antibodies, antibody fragments and single chain antibodies. Said nucleic acids are selected from deoxyribonucleic acids (DNA), ribonucleic acids (RNA), aptamers and peptidic nucleic acids (PNA).

Besides the compound having the general formula I or the conjugate thereof, the composition according to the present disclosure may also comprise other components required for staining biological samples, such as solvents, osmotic pressure regulating agents, pH regulating agents and surfactants. The composition according to the present disclosure may exist in the form of an aqueous solution, or in other forms suitable to formulate it into a solution using water prior to usage.

Application of the Compound or Composition of the Present Disclosure

The present disclosure further provides a method for staining biological samples using the above-said compound having the general formula I, or the composition comprising the above-said compound having the general formula I, said method comprising the step of contacting the above-said compound having the general formula I or the conjugate thereof, or the composition comprising the above-said compound having the general formula I with the biological samples. The term "contacting" as used herein may include contact in a solution or in a solid phase.

Characteristics

From the above description and the common knowledge familiar to those skilled in the art, the various characteristics of the compound according to the present disclosure will be appreciated, which may include but are not limited to the following: (1) a maximum excitation wavelength of about 640 nm, which may not change as a function of temperature and which matches the wavelength of the red semiconductor laser used; (2) when forming a complex with a nucleic acid, the dye/nucleic acid complex has an emission wavelength in the range of 600 nm to 900 nm in the near-infrared region, which avoids interference from the background fluorescence of the organisms per se and helps to improve the accuracy of the detection results; (3) good light illumination stability; (4) the ability to be used in the flow cytometer as the staining agent for the erythroblasts in the blood; (5) the characteristic of being easily degraded in aqueous solutions, and thus being more favorable to both the operators of the instrument and to the environment.

EXAMPLES

The present disclosure is further illustrated by the following particular examples to which or by which the present disclosure is not limited, as is appreciated by one skilled in the art.

Example 1

Synthesis of Dye-1

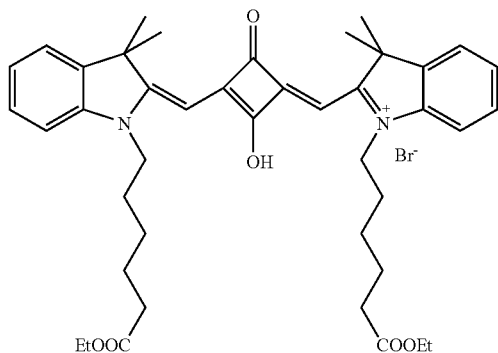

0.1 mol of 2,3,3-trimethylindole, 0.25 mol of ethyl 6-bromohexanoate and 25 mL of o-dichlorobenzene which was used as a solvent were added into a 100 mL 3-neck flask equipped with a reflux condenser and a magnetic stirrer with heating, and the mixture was reacted under reflux in an argon atmosphere for 24 hours. The reaction system was cooled to room temperature before a suitable amount of ethyl acetate was added therein. A crude product was precipitated out by ultrasonic vibration, which was triturated in ethyl acetate and then was filtered to obtain a dark brown-reddish block-like mass which was directly used in the next step of reaction.

0.01 mol of the brown-reddish product, 0.005 mol of squaric acid, and 8 mL of benzene, 6 mL of n-butanol and 6 mL of pyridine which were used as solvents were added together into a 50 mL 3-neck flask, and the mixture was stirred and heated to reflux in an argon atmosphere for 6 hours. Then the reaction was stopped and cooled to room temperature. The product was precipitated out by adding an excess amount of ethyl ether, filtered, washed with a suitable amount of ethyl ether, and dried to obtain a dark blue solid. The dark blue solid was purified by silica gel column chromatography eluting with a gradient of ethyl acetate: petroleum ether (5:0~5:1). The blue fractions were collected and the solvents therein were removed by rotary evaporation. The resulting residue was dried in a vacuum drying chamber at 45° C. for 24 hours to afford the title compound as a blue solid having a golden metallic luster, with a yield of 33%.

Maximum absorption peak: 637 nm (methanol/ethylene glycol)

MS (EI) $C_{42}H_{53}BrN_2O_6$ m/z: 681.9 $[M-Br]^+$.

Example 2

Synthesis of Dye-2

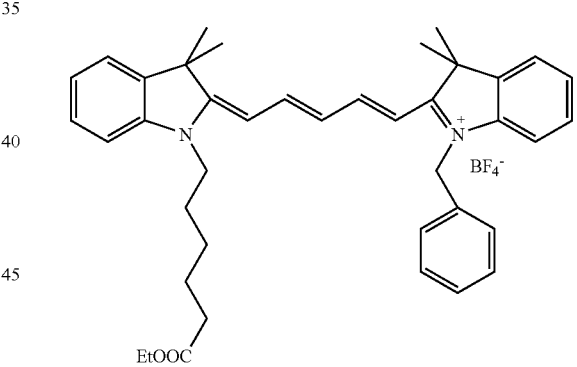

0.002 mol of 1-benzyl-2,3,3-trimethyl-3H-indoline hydrochloride and 0.0022 mol of malondialdehyde bis(phenylimine)monohydrochloride were accurately weighed and added into a 25 mL 3-neck flask, and 4 mL of acetic acid and 4 mL of acetic anhydride were added respectively. The mixture was stirred and heated to reflux in an argon atmosphere for 4 hours. Then the mixture was cooled to room temperature. The solvents were partly removed by rotary evaporation. The crude product was precipitated out by adding an excess amount of ethyl ether and then was filtered to obtain solid. The solid was showered with a small amount of ethyl acetate three times to remove the unreacted malondialdehyde bis(phenylimine)monohydrochloride, and yield a brown solid for next step reaction.

0.001 mol of the brown product and 0.0012 mol of 1-(hexyl acetate)-2,3,3-trimethyl-3H-indolinium bromide were added into a 3-neck flask, and 3 mL of acetic anhydride and 3 mL of pyridine were added respectively as the solvents. The mixture was stirred and heated to reflux in an argon atmosphere for 40 minutes. Then a solution of 0.0011 mol of sodium borofluoride in 3 mL of DMF was added followed by further stirring and heating for 15 minutes. The mixture was cooled to room temperature and an excess amount of ethyl ether was added to precipitate out the crude product, which was filtered before drying to afford a dark blue solid. The dark blue solid was purified by silica gel column chromatography eluting with a gradient of dichloromethane: methanol (5:0~5:1). The blue fractions were collected and the solvents therein were removed by rotary evaporation. The resulting residue was dried in a vacuum drying chamber at 45° C. for 24 hours to afford the title compound with a yield of 36%.

Maximum absorption peak: 641 nm (methanol/ethylene glycol).

MS (EI) $C_{40}H_{47}BF_4N_2O_2$ m/z: 587.8 $[M-BF_4]^+$.

Example 3

Synthesis of Dye-3

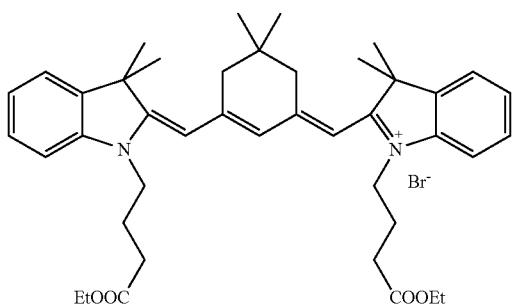

0.05 mol of 2,3,3-trimethylindole, 0.20 mol of ethyl 4-bromobutyrate and 10 mL of toluene which was used as a solvent were added into a 250 mL 3-neck flask equipped with a reflux condenser and a magnetic stirrer with heating, and the mixture was reacted under reflux in an argon atmosphere for 24 hours. The reaction system was cooled to room temperature before a suitable amount of ethyl acetate was added therein. The crude product was precipitated out by ultrasonic vibration, which was triturated with ethyl acetate and then filtered to obtain a dark brown-reddish block-like mass which was directly used in the next step of reaction.

0.08 mol of the brown-reddish mass, 0.004 mol of isophorone, and 5 mL of acetic anhydride and 5 mL of pyridine were added together into a 25 mL 3-neck flask, wherein acetic anhydride and pyridine were used as solvents, and then the mixture was stirred and heated to reflux in an argon atmosphere for 4 hours. Then the mixture was cooled to room temperature. The crude product was precipitated out by adding an excess amount of ethyl ether, which was filtered, washed with a suitable amount of ethyl ether, and dried to obtain a dark blue solid. The dark blue solid was purified by silica gel column chromatography eluting with a gradient of ethyl acetate: petroleum ether (100:0~100:15). The blue fractions were collected and the solvents therein were removed by rotary evaporation. The resulting residue was dried in a vacuum drying chamber at 45° C. for 24 hours to afford the title compound with a yield of 40%.

Maximum absorption peak: 639 nm (methanol/ethylene glycol).

MS (EI) $C_{42}H_{55}BrN_2O_4$ m/z: 651.9 $[M-Br]^+$.

Example 4

Synthesis of Dye-4

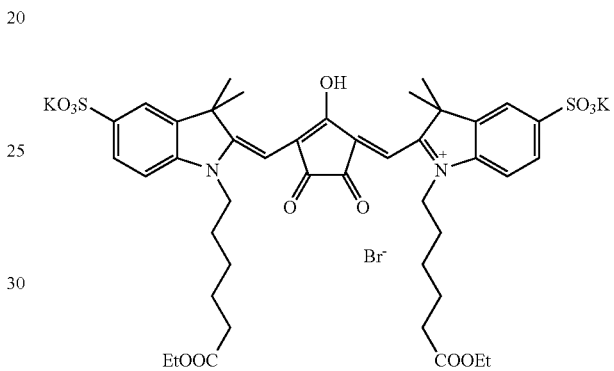

0.1 mol of potassium 5-sulfo-2,3,3-trimethylindole, 0.25 mol of ethyl 6-bromohexanoate and 25 mL of o-dichlorobenzene which was used as solvent were added into a 100 mL 3-neck flask equipped with a reflux condenser and a magnetic stirrer with heating, and the mixture was reacted under reflux in an argon atmosphere for 36 hours. The reaction system was cooled to room temperature before a suitable amount of ethyl ether was added therein. The crude product was precipitated out by ultrasonic vibration, which was triturated in ethyl acetate and then filtered to obtain a dark brown-reddish block-like mass, which was directly used in the next step of reaction.

0.08 mol of the dark brown-reddish mess, 0.004 mol of crocic acid and 6 mL of benzene, 4 mL of n-butanol and 4 mL of pyridine were added together into a 50 mL 3-neck flask, wherein benzene, n-butanol and pyridine were used as solvents, and then the mixture was stirred and heated to reflux in an argon atmosphere for 6 hours. Then the mixture was cooled to room temperature. The crude product was precipitated out by adding an excess amount of ethyl ether, which was filtered, washed with a suitable amount of ethyl ether, and dried to obtain a dark blue-green solid. The dark blue-green solid was purified by reverse-phase $C_{18}$ silica gel column chromatography eluting with a gradient of methanol: water (0:100~1:4). The blue fractions were collected and the solvents therein were removed by rotary evaporation. The resulting residue was dried in a vacuum drying chamber at 45° C. for 24 hours to afford the title compound as a blue solid having a metallic luster, with a yield of 37%.

Maximum absorption peak: 637 nm (methanol/ethylene glycol).

MS (EI) $C_{43}H_{51}KN_2O_{13}S_2$ m/z: 868.1 [M-K].

Example 5

Synthesis of Dye-5

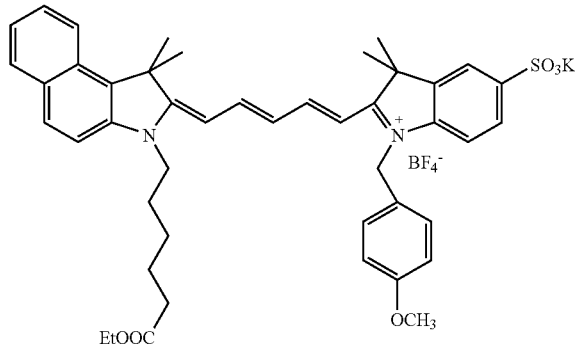

0.002 mol of potassium 5-sulfo-1-(4-methoxybenzyl)-2,3,3-trimethyl-3H-indoline hydrochloride and 0.0022 mol of malondialdehyde bis(phenylimine) monohydrochloride were accurately weighed and added into a 25 mL 1-neck flask, and 4 mL of acetic acid and 4 mL of acetic anhydride were added respectively. The mixture was stirred and heated to reflux in an argon atmosphere for 4 hours. Then the mixture was cooled to room temperature. The solvents were partly removed by rotary evaporation. The crude product was precipitated out by adding an excess amount of ethyl ether and filtered to obtain solid. The solid were showered with a small amount of ethyl acetate for three times to remove the unreacted condensing agent, and yield a brown-yellowish solid.

0.001 mol of the brown-yellowish solid and 0.0012 mol of 3-(hexyl acetate)-1,1,2-trimethyl-1H-benzo[e]indolium bromide were added into a 3-neck flask, and 4 mL of acetic anhydride and 4 mL of pyridine were added respectively as the solvents. The mixture was stirred and heated to reflux in an argon atmosphere for 40 minutes. Then 3 mL of DMF solution containing 0.0012 mol of sodium borofluoride was added and then the mixture was further heated for 20 minutes. The mixture was cooled to room temperature and an excess amount of ethyl ether was added to precipitate out crude product, which was filtered before drying to afford a dark blue solid. The dark blue solid was purified by silica gel column chromatography eluting with a gradient of dichloromethane:methanol (5:0~5:1). The blue fractions were collected and the solvents therein were removed by rotary evaporation. The resulting residue was dried in a vacuum drying chamber at 45° C. for 24 hours to afford the title compound as a blue solid having a metallic luster, with a yield of 29%.

Maximum absorption peak: 642 nm (methanol/ethylene glycol).

MS (EI) $C_{45}H_{50}BF_4KN_2O_6S$ m/z:747.0 $[M-BF_4]^+$.

Example 6

Synthesis of Dye-6

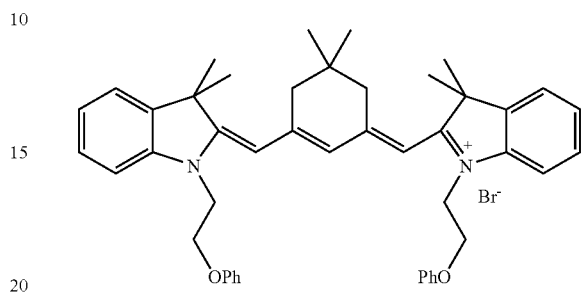

0.05 mol of 2,3,3-trimethylindole, 0.10 mol of 2-bromoethoxybenzene and 10 mL of o-dichlorobenzene which was used as a solvent were added into a 250 mL 3-neck flask equipped with a reflux condenser and a magnetic stirrer with heating, and the mixture was reacted under reflux in an argon atmosphere for 28 hours. The reaction system was cooled to room temperature before a suitable amount of ethyl acetate was added therein. The crude product was precipitated out by ultrasonic vibration, which was triturated in ethyl acetate and then filtered to obtain a brown-reddish block-like mass which was directly used in the next step of reaction.

0.005 mol of the brown-reddish mass, 0.0025 mol of isophorone, and 4 mL of benzene, 3 mL of n-butanol and 3 mL of pyridine were added together into a 50 mL 3-neck flask, wherein benzene, n-butanol and pyridine were used as solvents, and then the mixture was stirred and heated to reflux in an argon atmosphere for 6 hours. Then the mixture was cooled to room temperature. The crude product was precipitated out by adding an excess amount of ethyl ether, filtered, washed with a suitable amount of ethyl ether, and dried to obtain a dark blue solid. The dark blue solid was purified by silica gel column chromatography eluting with a gradient of ethyl acetate:petroleum ether (5:0~5:1). The blue fractions were collected and the solvents therein were removed by rotary evaporation. The resulting residue was dried in a vacuum drying chamber at 45° C. for 24 hours to afford the title compound with a yield of 33%.

Maximum absorption peak: 638 nm (methanol/ethylene glycol).

MS (El) $C_{46}H_{51}BrN_2O_2$ m/z: 663.9 $[M-Br]^+$.

Example 7

Determination of the Absorption Peaks of the Compounds Synthesized in the Above Examples of the Present Disclosure An amount of each of the compounds synthesized in the above examples was accurately weighed and completely dissolved in 2.5 mL of methanol/ethylene glycol (50:50 by volume) to prepare a 5 mM solution. 5 uL aliquots of the solution were each diluted in 2 mL of methanol/ethylene glycol solution and the dilutions were placed under a hermetic, light-proof condition at 0° C., 20° C., 40° C. and 60° C. respectively for 48 hours. The maximum absorption peak was detected using an UVmini-1240 UV-Vis Spectrophotometer. The absorption peaks for Dye-1 placed at different temperatures are as shown in FIG. 1. It can be seen from the figure that the positions of the maximum absorption peak did not shift as a function of temperature, which ensures a good match with the excitation wavelength of the laser.

Table 1 shows the values of the maximum absorption peak for Dye-1, Dye-2, Dye-4, Dye-5 and Dye-6 placed at different temperatures for 48 hours.

TABLE 1

| Temp. | Maximum absorption peak (nm) | | | | |
|---|---|---|---|---|---|
|  | Dye-1 | Dye-2 | Dye-4 | Dye-5 | Dye-6 |
| 0° C. | 637 | 641 | 637 | 642 | 638 |
| 20° C. | 637 | 641 | 637 | 642 | 638 |
| 40° C. | 637 | 641 | 637 | 642 | 638 |
| 60° C. | 637 | 641 | 637 | 642 | 638 |

The data in the above table indicate stability of the maximum absorption peak of the compounds synthesized in the above examples of the present disclosure which were placed at different temperatures for 48 hours.

Example 8

Figure 2:
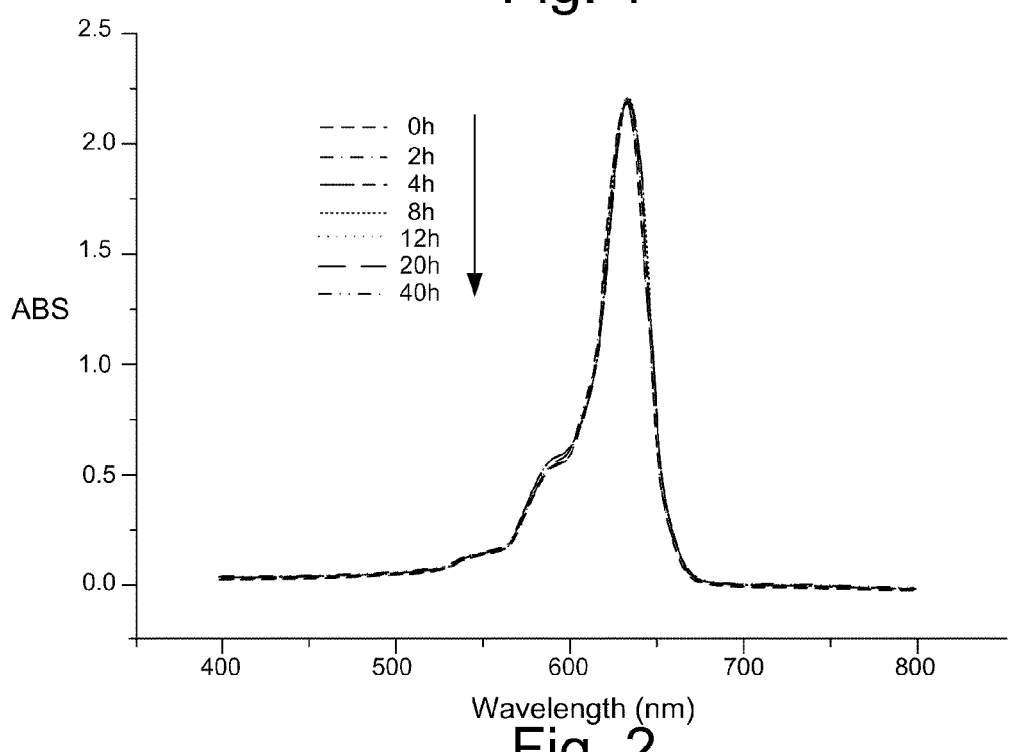
FIG. 2 shows absorption spectra of the exemplary Dye-1 compound in an alcohol solution after being illuminated for different periods of time. The instrument used is a UVmini-1240 UV-Vis Spectrophotometer.

Determination of the Light Stability of the Compounds Synthesized in the Above Examples of the Present Disclosure in an Ethanol Solution A certain amount of Dye-1 was dissolved in ethanol solution to prepare a dye solution at the concentration of $1 \times 10^{-5}$ M and placed into a sealable quartz cuvette. A 50 g/L sodium nitrite solution was placed in a rectangular glass jar to act as a cut-off filter that filters UV light with a wavelength under 400 nm. In addition, the sodium nitrite solution can also function as a cold trap to keep the temperature of the sample at common temperature. After measuring the initial absorbance of the sample, the 500 W iodine-tungsten lamp used as the light source was turned on to illuminate the sample 20 cm apart when timing was started. The sample was measured for absorbance after being illuminated for 2, 4, 8, 12, 20 and 40 hours respectively. As shown in FIG. 2, no obvious fading is seen after Dye-1 compound illuminated for periods of time, suggesting that the compound has a certain degree of light stability and can be stably stored in ethanol solution. The equipment used was an UVmini-1240 UV-Vis Spectrophotometer.

Example 9

Figure 3:
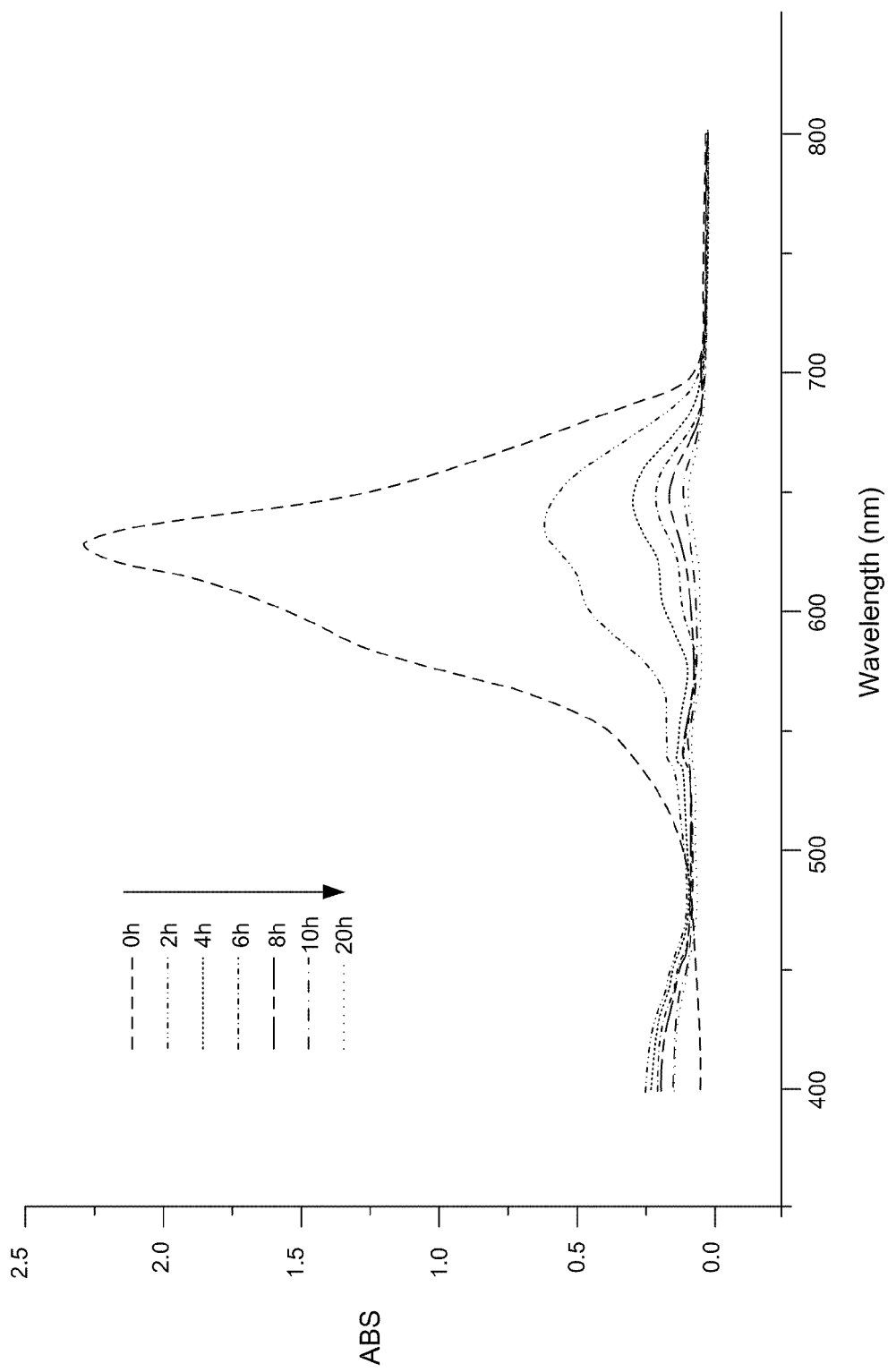
FIG. 3 shows absorption spectra of the exemplary Dye-1 compound in a phosphate buffer after being illuminated for different periods of time. The instrument used is a UVmini-1240 UV-Vis Spectrophotometer.

Determination of the Light Stability of the Compounds Synthesized in the Above Examples of the Present Disclosure in a Phosphate Buffer Saline (PBS) Solution A certain amount of Dye-1 was dissolved in phosphate buffer saline (PBS) solution to prepare a dye solution at the concentration of $1 \times 10^{-5}$ M and placed into a sealable cuvette. A 50 g/L sodium nitrite solution was placed in a rectangular glass jar to act as a cut-off filter that filters UV light with a wavelength under 400 nm. In addition, the sodium nitrite solution can also function as a cold trap to keep the temperature of the sample at common temperature. After measuring the initial absorbance of the sample, the 500 W iodine-tungsten lamp used as the light source was turned on to illuminate the sample 20 cm apart when timing was started. The sample was measured for absorbance after being illuminated for 2, 4, 6, 8, 10 and 20 hours respectively. As shown in FIG. 3, the compound fades by 73% after 2-hour illumination in the PBS solution, by 87% after 4-hour illumination, and by more than 90% after 6-hour illumination, suggesting that the compound is less stable in the PBS solution and will be degraded into colorless substances in a short time. The equipment used was an UVmini-1240 UV-Vis Spectrophotometer.

This example, in conjunction with Example 8, demonstrates that the compounds according to the present disclosure, have a good light stability in the alcohol solution, which permits stable storage and long shelf-life of the compounds. The compounds having been used, in the PBS solution, exhibit a favorable light instability however, and can be degraded into colorless substances in a short time, demonstrating their favorability to the operators of the instrument and to the environment.

Example 10

Dye-1 Compound as an Erythroblast Detection Reagent

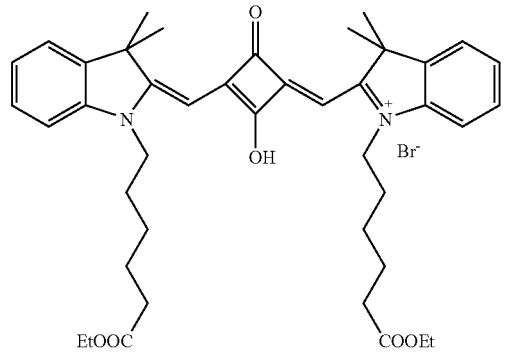

Figure 4:
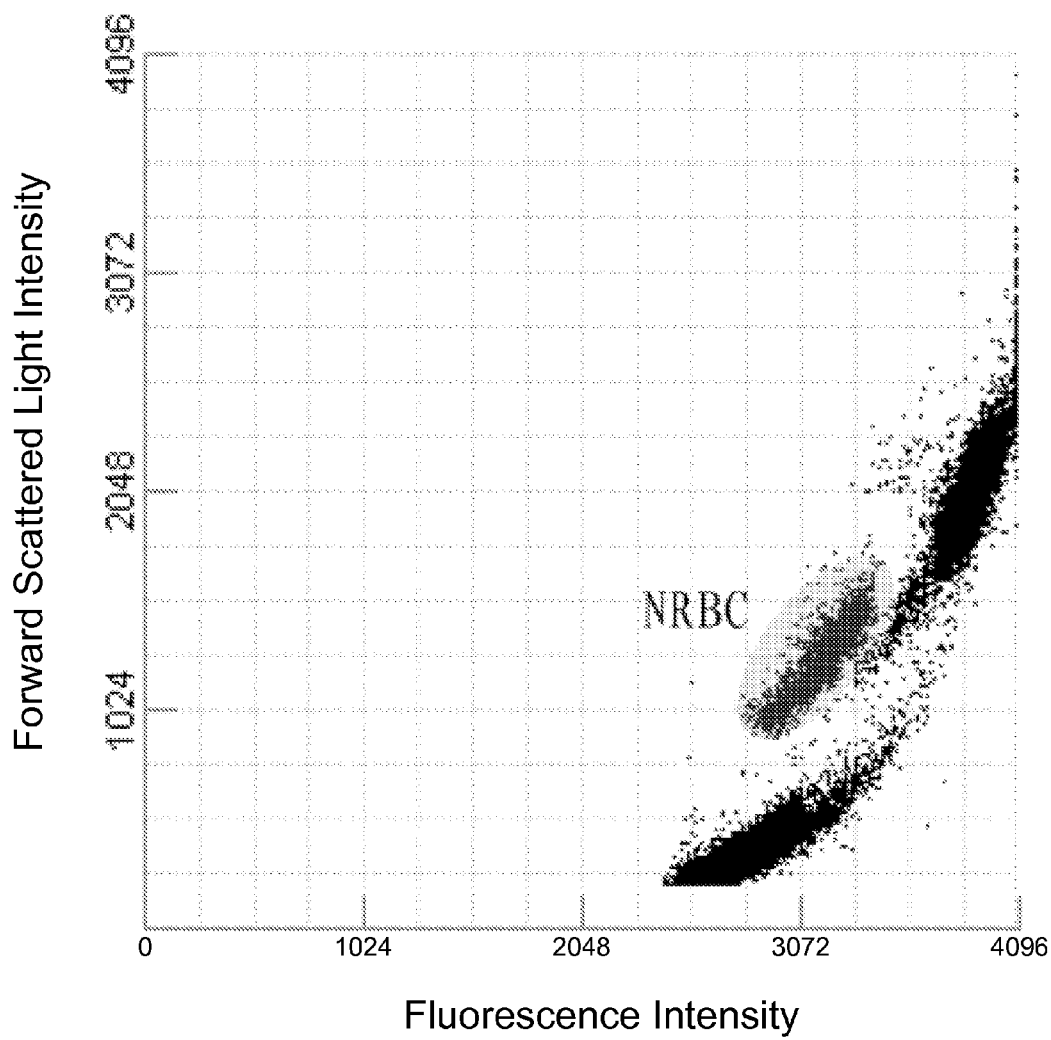
FIG. 4 shows a scattergram of forward scattered light intensity versus fluorescence intensity of blood measured using the Dye-1 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-1 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 4 shows the comparison of the fluorescence of the erythroblasts with that of the leukocytes, with the erythroblasts comprising 5.9% of the total leukocytes.

Example 11

Dye-2 Compound as an Erythroblast Detection Reagent

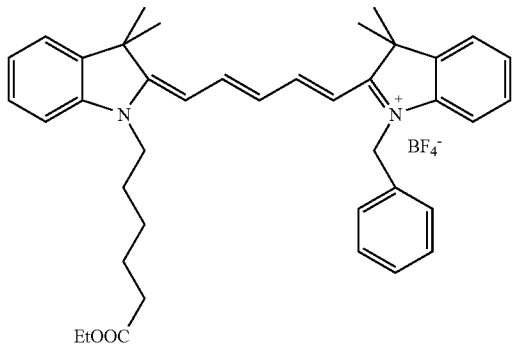

Figure 5:
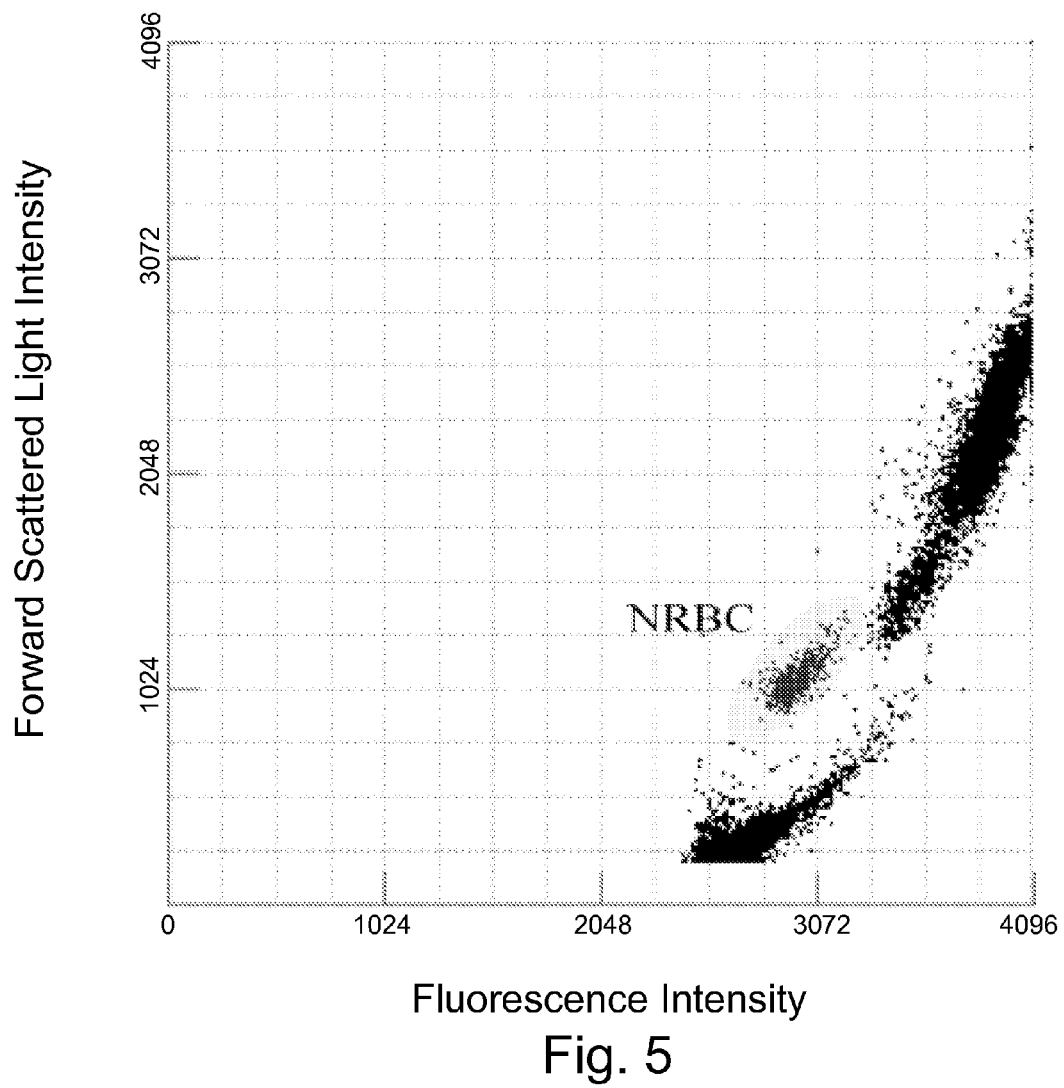
FIG. 5 shows a scattergram of forward scattered light intensity versus fluorescence intensity of blood measured using the Dye-2 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-2 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 5 shows the comparison of the fluorescence of the erythroblasts with that of the leukocytes, with the erythroblasts comprising 3.2% of the total leukocytes.

Example 12

Dye-3 Compound as an Erythroblast Detection Reagent

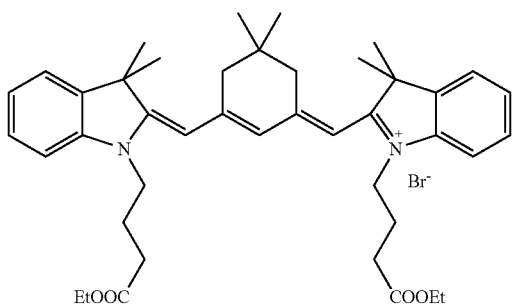

Figure 6:
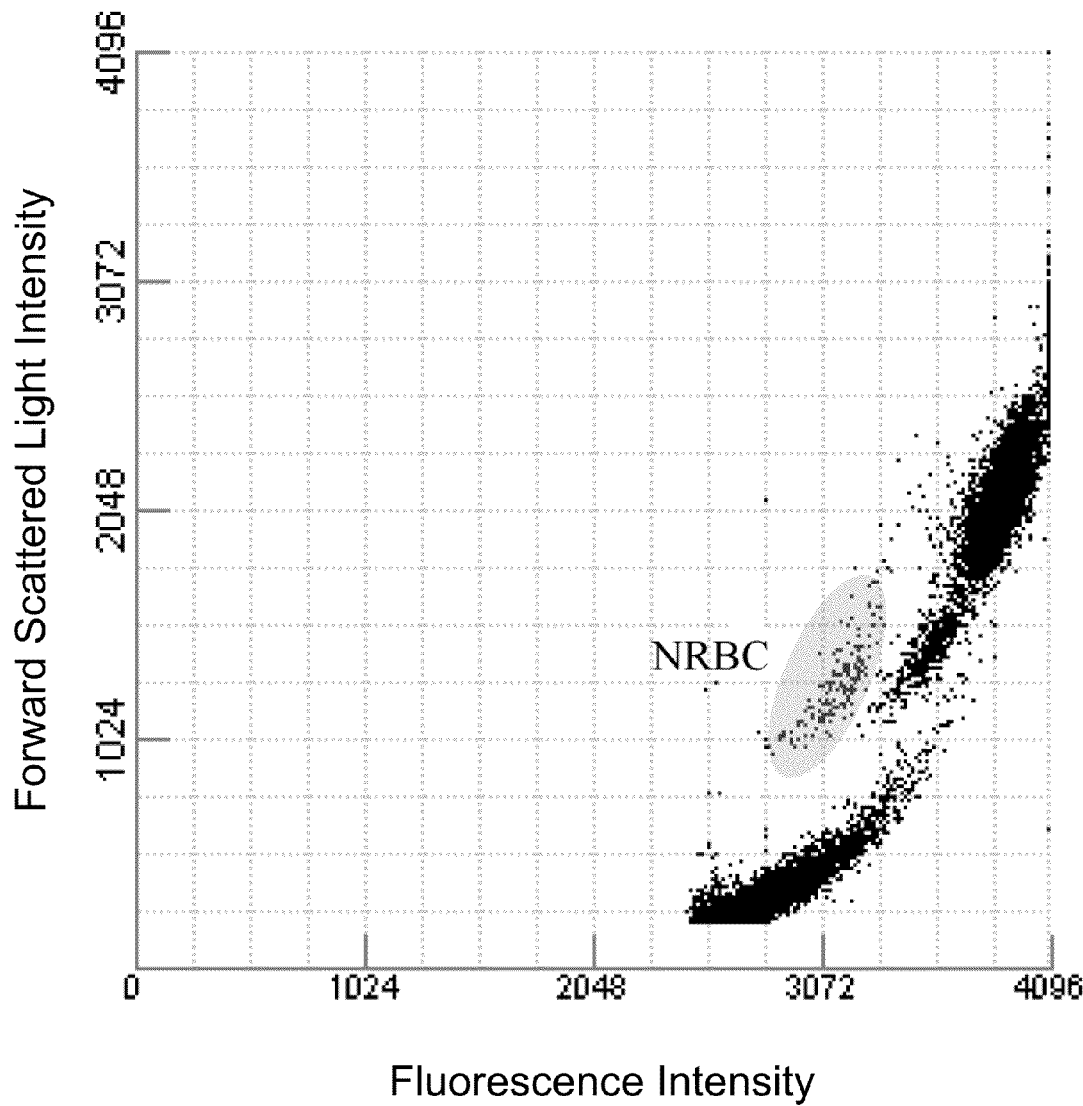
FIG. 6 shows a scattergram of forward scattered light intensity versus fluorescence intensity of blood measured using the Dye-3 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-3 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 6 shows the comparison of the fluorescence of the erythroblasts with that of the leukocytes, with the erythroblasts comprising 1.3% of the total leukocytes.

Example 13

Dye-4 Compound as an Erythroblast Detection Reagent

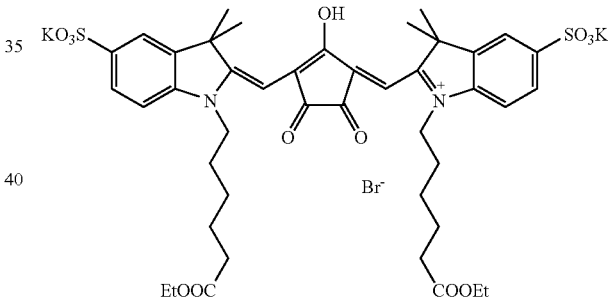

Figure 7:
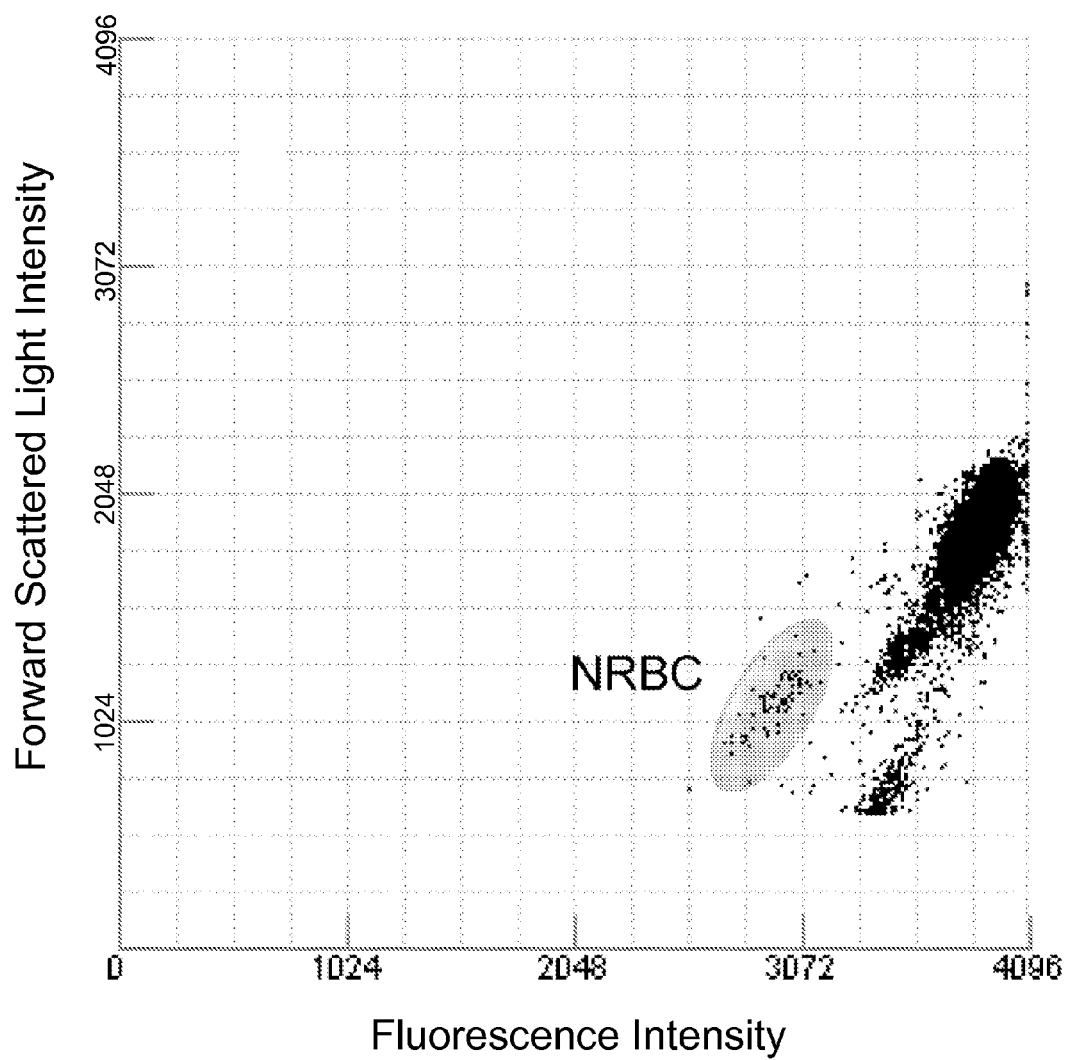
FIG. 7 shows a scattergram of forward scattered light intensity versus fluorescence intensity of blood measured using the Dye-4 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-4 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 7 shows the comparison of the fluorescence of the erythroblasts with that of the leukocytes, with the erythroblasts comprising 0.9% of the total leukocytes.

Example 14

Dye-5 Compound as an Erythroblast Detection Reagent

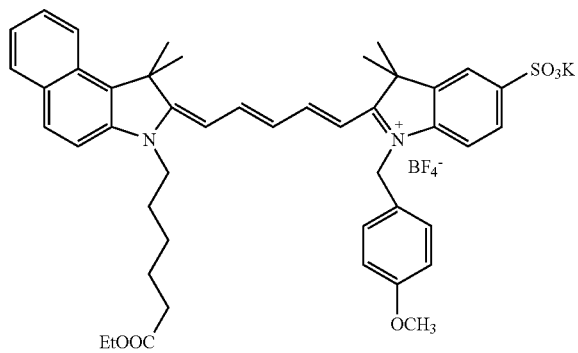

Figure 8:
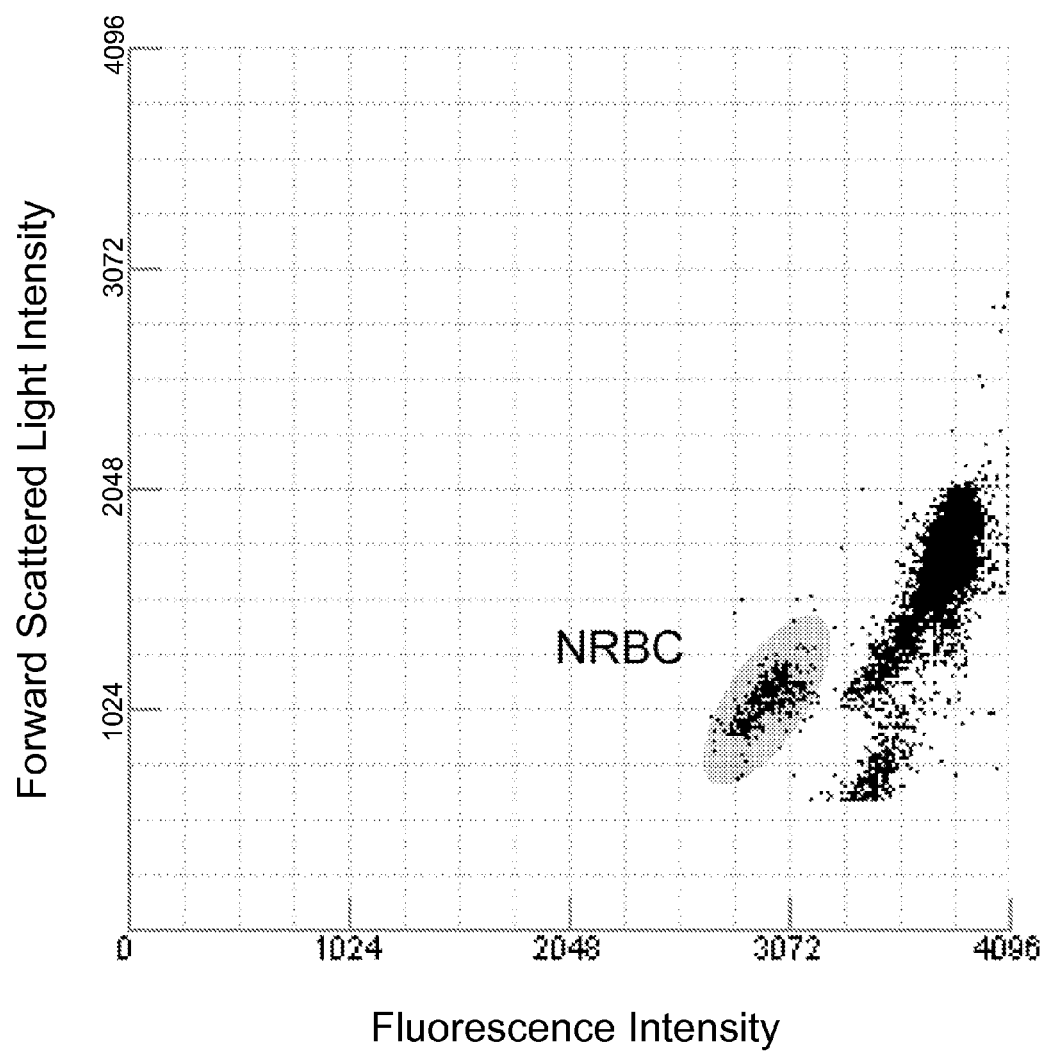
FIG. 8 shows a scattergram of forward scattered light intensity versus fluorescence intensity of blood measured using the Dye-5 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-5 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 8 shows the comparison of the fluorescence of the erythroblasts with that of the leukocytes, with the erythroblasts comprising 2.5% of the total leukocytes.

Example 15

Dye-6 Compound as an Erythroblast Detection Reagent

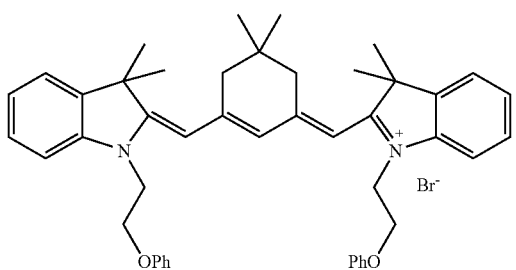

Figure 9:
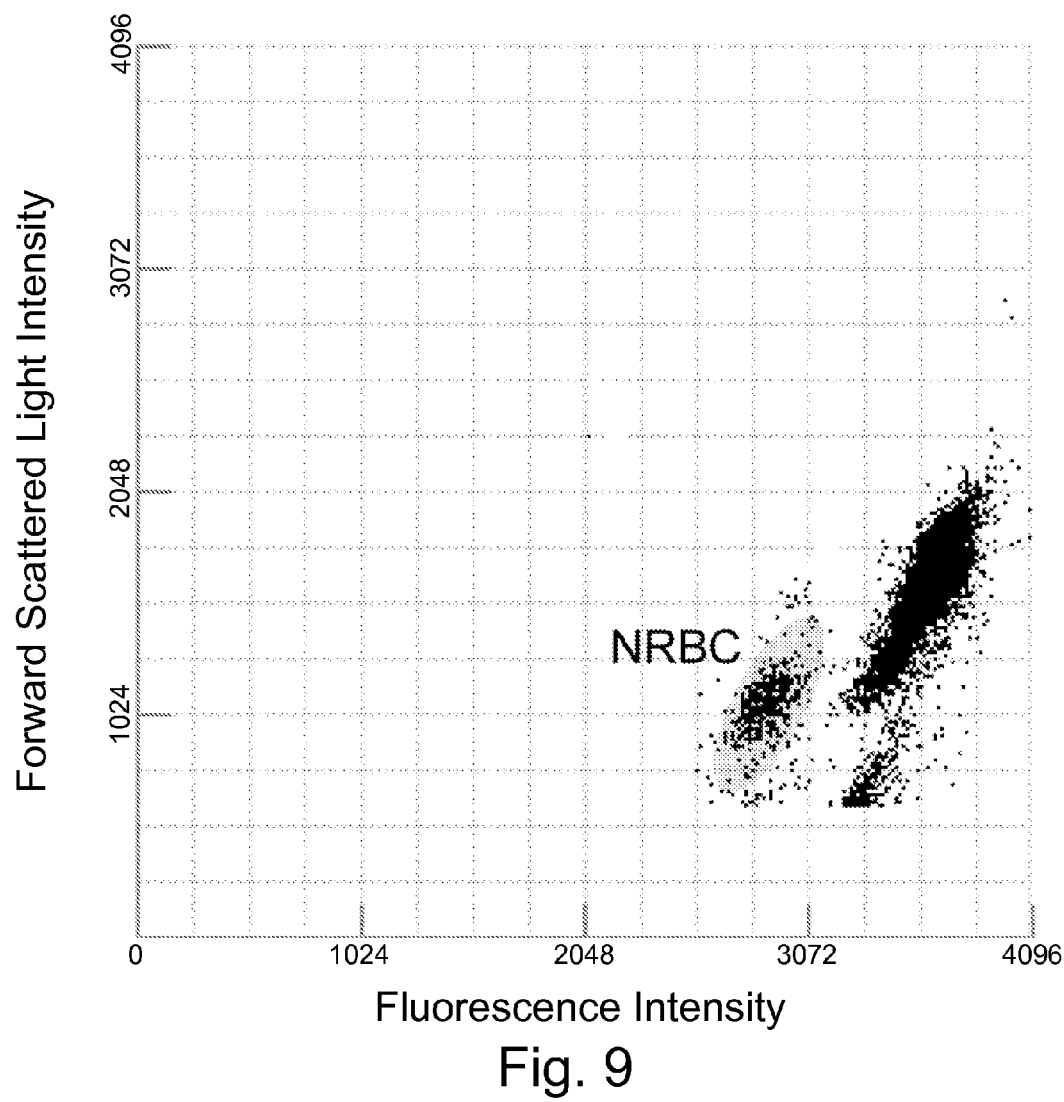
FIG. 9 shows a scattergram of forward scattered light intensity versus fluorescence intensity of blood measured using the Dye-6 compound as the detection reagent for erythroblasts. The abscissa represents fluorescence intensity and the ordinate represents forward scattered light intensity.

10 μL of anticoagulant-treated blood was added into 2 mL of an erythroblast detection reagent containing the Dye-6 compound to prepare a test sample. Then the sample was sucked into a properly adapted flow cytometer (Chinese Patent CN 101000306A, Shenzhen Mindray Bio-medical Electronics Co., Ltd. Shenzhen, People's Republic of China) and detected for forward low-angle scattered light intensity and fluorescence intensity. In terms of the fluorescence intensity and the scattered light intensity, the erythroblasts and leukocytes in the test sample were identified, differentiated and counted, and the ratio of the respective cells was calculated. The ratio of erythroblasts is typically expressed as the number of erythroblasts in every 100 leukocytes, in "number of erythroblasts/100 leukocytes". FIG. 9 shows the comparison of the fluorescence of the erythroblasts with that of the leukocytes, with the erythroblasts comprising 2.3% of the total leukocytes.

Although the present disclosure has been illustrated by way of the above embodiments and particular examples thereof, it will be appreciated by those skilled in the art that various changes, alterations and modifications may be made to the present disclosure without departing from the spirit and scope of the present disclosure as defined by the appended claims.

The invention claimed is:

1. A compound having the general formula I:

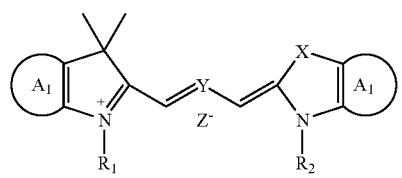

wherein $R_1$ and $R_2$ are each independently selected from at least one of the following: $C_{1-18}$alkylCOOR$_6$, $C_{1-18}$alkylOR$_6$ and benzyl, wherein said benzyl is optionally substituted with at least one of the following: a substituent selected from halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;

$R_6$ in each occurrence is independently selected from at least one of the following: $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is

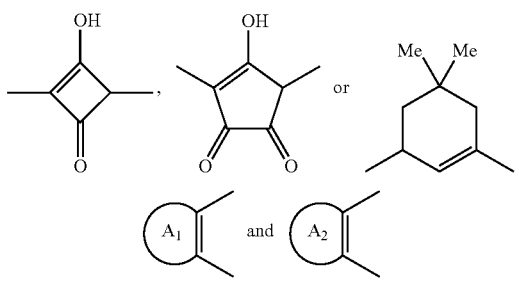

are each independently selected from

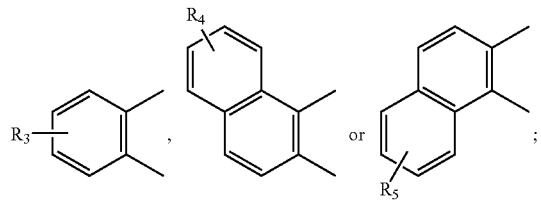

R$_3$, R$_4$ and R$_5$ are each independently selected from at least one of the following: H, halogen, cyano, hydroxyl, C$_{1-18}$alkyl, C$_{1-18}$alkylsulphonyl, sulphonyl and C$_{1-5}$alkylCOOR$_7$;

R$_7$ is H or C$_{1-6}$alkyl; and

Z$^-$ is an anion.

2. The compound according to claim 1, wherein R$_1$ and R$_2$ are each independently selected from at least one of the following: C$_{1-6}$alkylCOOR$_6$, C$_{1-6}$alkylOR$_6$ and benzyl, provided that R$_1$ and R$_2$ are not all simultaneously benzyl.

3. The compound according to claim 1, wherein R$_6$ in each occurrence is independently selected from C$_{1-6}$alkyl or phenyl.

4. The compound according to claim 1, wherein R$_3$, R$_4$ and R$_5$ are each independently selected from at least one of the following: H, halogen, cyano, hydroxyl, C$_{1-6}$alkyl, C$_{1-6}$alkylsulphonyl, sulphonyl or C$_{1-5}$alkylCOOR$_7$.

5. The compound according to claim 1, wherein X is C(CH$_3$)$_2$, O or S.

6. The compound according to claim 1, wherein

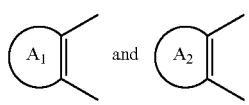

are each independently selected from

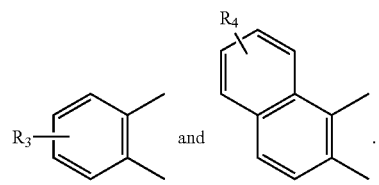

7. The compound according to claim 1, wherein Z$^-$ is selected from halogen ions, ClO$_4^-$, PF$_6^-$, CF$_3$SO$_3^-$, BF$_4^-$, acetate or p-toluenesulfonate anions.

8. A compound selected from:

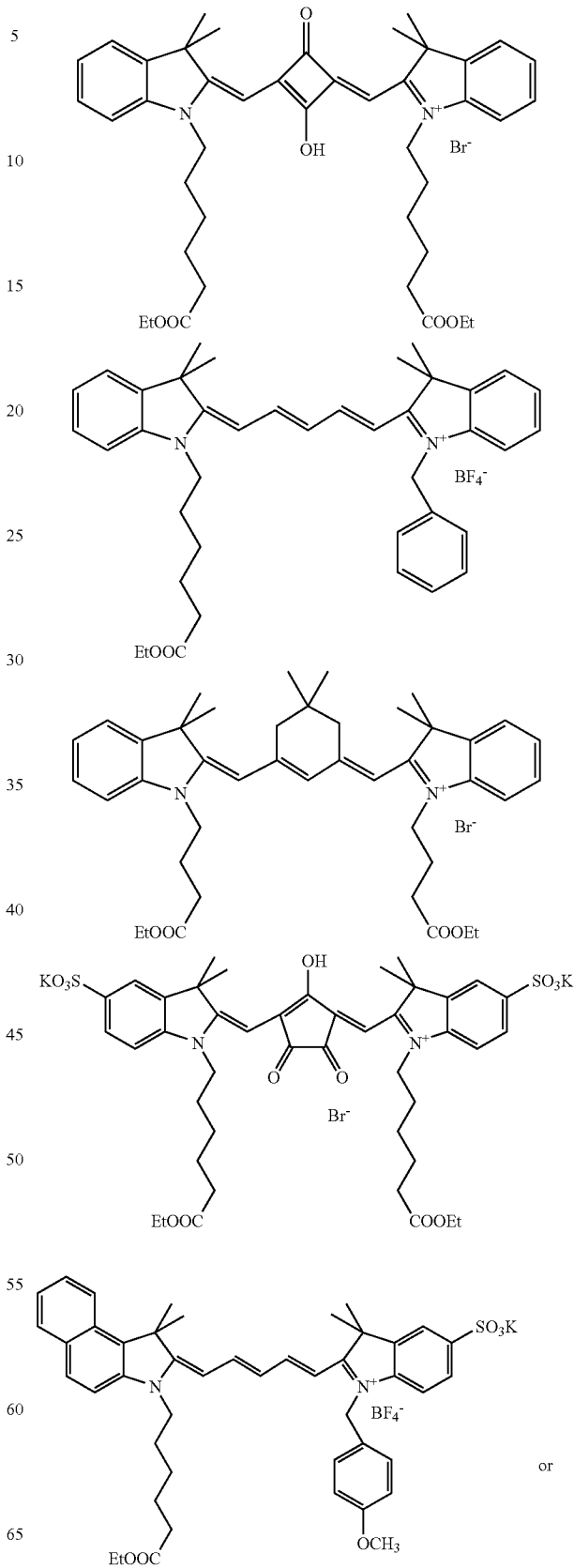

-continued

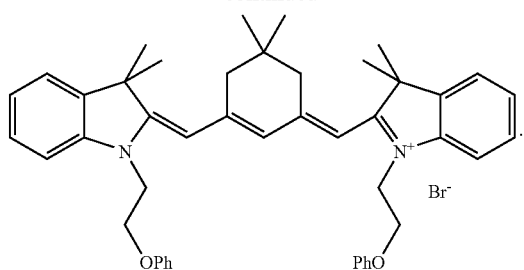

9. A conjugate comprising the compound according to claim 1.

10. A composition for staining biological samples, said composition comprising the compound according to claim 1 or a conjugate thereof.

11. The composition according to claim 10, wherein said biological samples are selected from peptides, proteins, nucleic acids, and erythroblasts in blood.

12. The composition according to claim 11, wherein said proteins are selected from antibodies, antibody fragments and single chain antibodies.

13. The composition according to claim 11, wherein said nucleic acids are selected from deoxyribonucleic acids (DNA), ribonucleic acids (RNA), aptamers and peptidic nucleic acids (PNA).

14. A method of using the compound of claim 1, comprising: staining a biological sample with the compound of claim 1, or a conjugate thereof or a composition containing the compound of claim 1.

15. A compound having the general formula I:

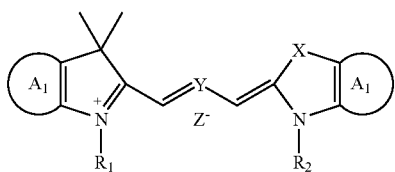

I wherein $R_1$ and $R_2$ are each independently selected from at least one of the following: $C_{1-18}$alkylCOOR$_6$, $C_{1-18}$alkylOR$_6$ and benzyl, wherein said benzyl is optionally substituted with at least one of the following: a substituent selected from halogen, hydroxyl, sulfhydryl, cyano, nitro, alkyl, aryl, alkyloxy, heterocyclyl, haloalkyl, amino, alkylamino, amido and carboxyl, provided that $R_1$ and $R_2$ are not all simultaneously benzyl;

$R_6$ in each occurrence is independently selected from at least one of the following: H, $C_{1-18}$alkyl or phenyl, wherein said phenyl is optionally substituted with a substituent selected from at least one of the following: halogen, hydroxyl, sulfhydryl, cyano, nitro, alkyl, aryl, alkyloxy, heterocyclyl, haloalkyl, amino, alkylamino, amido and carboxyl;

X is $CH_2$, $C(CH_3)_2$, O, S or Se;

Y is

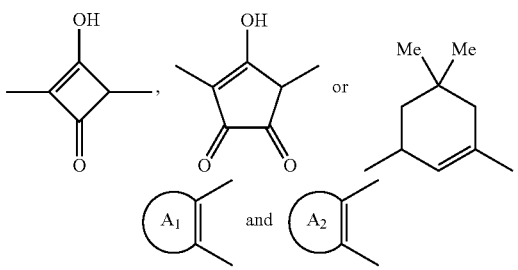

are each independently selected from

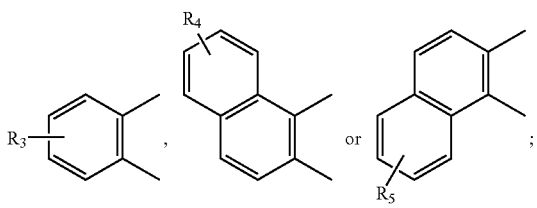

$R_3$, $R_4$ and $R_5$ are each independently selected from at least one of the following: H, halogen, cyano, hydroxyl, $C_{1-18}$alkyl, $C_{1-18}$alkylsulphonyl, sulphonyl and $C_{1-5}$alkylCOOR$_7$;

$R_7$ is H or $C_{1-6}$alkyl; and $Z^-$ is an anion.

16. The compound according to claim 15, wherein $R_1$ and $R_2$ are each independently selected from at least one of the following: $C_{1-6}$alkylCOOR$_6$, $C_{1-6}$alkylOR$_6$ and benzyl, provided that $R_1$ and $R_2$ are not all simultaneously benzyl.

17. The compound according to claim 15, wherein $R_6$ in each occurrence is independently selected from H, $C_{1-6}$alkyl or phenyl.

18. The compound according to claim 15, wherein $R_3$, $R_4$ and $R_5$ are each independently selected from at least one of the following: H, halogen, cyano, hydroxyl, $C_{1-6}$alkyl, $C_{1-6}$alkylsulphonyl, sulphonyl or $C_{1-5}$alkylCOOR$_7$.

19. The compound according to claim 15, wherein X is $C(CH_3)_2$, O or S.

20. The compound according to claim 15, wherein

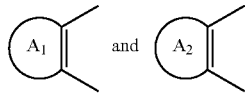

are each independently selected from

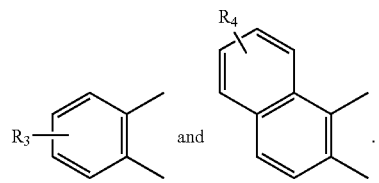

21. The compound according to claim 15, wherein $Z^-$ is selected from halogen ions, $ClO_4^-$, $PF_6^-$, $CF_3SO_3^-$, $BF_4^-$, acetate or p-toluenesulfonate anions.

22. A conjugate comprising the compound according to claim 15.

23. A composition for staining biological samples, said composition comprising the compound according to claim 15 or a conjugate thereof.

24. The composition according to claim 23, wherein said biological samples are selected from peptides, proteins, nucleic acids, and erythroblasts in blood.

25. The composition according to claim 24, wherein said proteins are selected from antibodies, antibody fragments and single chain antibodies.

26. The composition according to claim 24, wherein said nucleic acids are selected from deoxyribonucleic acids (DNA), ribonucleic acids (RNA), aptamers and peptidic nucleic acids (PNA).

27. A method of using the compound of claim 15, comprising:
   staining a biological sample with the compound of claim 15, or a conjugate thereof or a composition containing the compound of claim 15.

* * * * *